(12) United States Patent
Kamakura et al.

(10) Patent No.: US 8,377,476 B2
(45) Date of Patent: Feb. 19, 2013

(54) BUTENAFINE HYDROCHLORIDE-CONTAINING AQUEOUS PATCH

(75) Inventors: Takashi Kamakura, Kita-gun (JP); Takefumi Hoshikawa, Higashikagawa (JP); Yukiko Inamoto, Takamatsu (JP); Kayo Tanigawa, Hirakata (JP)

(73) Assignee: Teikoku Seiyaku Co., Ltd., Higashikagawa-shi (JP)

( * ) Notice: Subject to any disclaimer, the term of this patent is extended or adjusted under 35 U.S.C. 154(b) by 0 days.

(21) Appl. No.: 12/936,815

(22) PCT Filed: Mar. 24, 2009

(86) PCT No.: PCT/JP2009/055853
§ 371 (c)(1),
(2), (4) Date: Dec. 28, 2010

(87) PCT Pub. No.: WO2009/125667
PCT Pub. Date: Oct. 15, 2009

(65) Prior Publication Data
US 2011/0097407 A1    Apr. 28, 2011

(30) Foreign Application Priority Data
Apr. 8, 2008    (JP) .................................. 2008-100041

(51) Int. Cl.
*A61F 13/00* (2006.01)
*A61K 9/70* (2006.01)

(52) U.S. Cl. .......................... 424/486; 424/443; 424/449
(58) Field of Classification Search .................. None
See application file for complete search history.

(56) References Cited

U.S. PATENT DOCUMENTS

| | | | | |
|---|---|---|---|---|
| 6,017,920 A | * | 1/2000 | Kamishita et al. | 514/254.07 |
| 6,143,764 A | * | 11/2000 | Kubo et al. | 514/312 |
| 2003/0180347 A1 | * | 9/2003 | Young et al. | 424/449 |
| 2007/0099932 A1 | * | 5/2007 | Shirouzu et al. | 514/254.07 |
| 2009/0099202 A1 | * | 4/2009 | Shirouzu et al. | 514/254.07 |
| 2011/0269794 A1 | * | 11/2011 | Shirouzu et al. | 514/312 |

* cited by examiner

*Primary Examiner* — Robert A Wax
*Assistant Examiner* — Olga V Tcherkasskaya
(74) *Attorney, Agent, or Firm* — Crowell & Moring LLP

(57) ABSTRACT

Disclosed is a water-based adhesive skin patch which has excellent storage stability, can achieve excellent accumulation of butenafine hydrochloride contained therein on a patched area such as the skin and a nail, and has a high therapeutic effect. Specifically disclosed is a water-based adhesive skin patch containing butenafine hydrochloride, which is characterized by containing butenafine hydrochloride, glycol salicylate and propylene glycol in a water-containing gel ointment. Specifically, butenafine hydrochloride is dissolved in a mixed solution of glycol salicylate and propylene glycol, and the resulting solution is dispersed in a water-containing gel. Particularly, the mixing ratio of glycol salicylate to propylene glycol is 1:2 to 1:30.

3 Claims, 1 Drawing Sheet

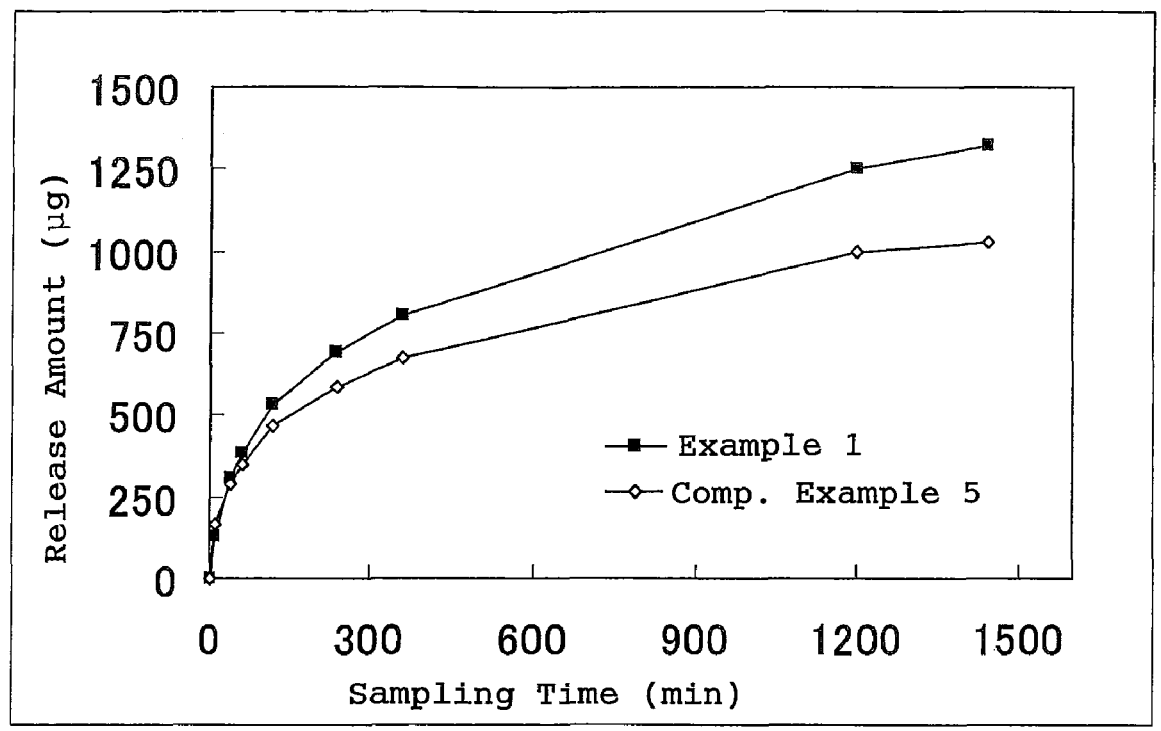

BUTENAFINE HYDROCHLORIDE-CONTAINING AQUEOUS PATCH

TECHNICAL FIELD

The present invention relates to a butenafine hydrochloride-containing aqueous patch which provides excellent adherence and retention of butenafine hydrochloride blended therein on the application sites and have excellent storage stability, and exerts an antifungal effect for an extended period of time.

BACKGROUND ART

Ointments, creams, or liquid formulations which include various antifungal agents have been developed for the treatment of tinea or candidiasis and are commercially available. However, these dosage forms have a short duration of effective drug concentration at the application sites and require 2 to 3 applications per day, and therefore patient compliance with treatments using them has been poor. To compensate for this disadvantage, transdermal formulations which include various antifungal agents have been under investigation.

For example, Patent Documents 1 and 2 disclose patches which include antifungal agents blended in an acrylic or a rubber-base adhesive. Patent Document 3 discloses a therapeutic composition for tinea unguium which includes omoconazole nitrate or butenafine hydrochloride blended in a base consisting of a hydrophobic film component and a solvent. Patent Document 4 discloses an external preparation which includes 2 or more a hydrophobic film-forming agents, water, a plasticizing agent, an antifungal agent, and alcohol. Furthermore, Patent Document 5 discloses a formulation which includes a hydrophilic film-forming substance, an antifungal agent, and water.

Furthermore, Patent Document 6 discloses an external composition which includes glycol salicylate in addition to an antifungal agent.

However, among these formulations, patches which include antifungal agents blended in an acrylic or a rubber-base adhesive did not provide sufficient drug release from the formulations or sufficient permeation of the drug into the application sites, resulting in insufficient drug retention on the application sites. In the nail lacquer or nail enamel formulations which include hydrophobic film-forming substances and hydrophilic film component substances, dehydration occurs at the application sites so that films are formed by volatilizing solvents contained in the compositions, resulting in unfavorable irritation. Furthermore, the formulations require the use of solvents or detergents to peel off, and thus they are less convenient.

Furthermore, formulations which include glycol salicylate in order to increase the permeability and retention of antifungal agents in the stratum corneum, for example, ointments, creams, gels, gel creams, and liquid preparations have the problems such as an inadequate therapeutic effect because of poor drug retention in the stratum corneum and short duration of effective drug concentration.

Among other antifungal agents, butenafine hydrochloride, which is a benzylamine antifungal agent, has been so far clinically used in the form of external solutions, creams, ointments, or sprays as therapeutic agents for treatment of dermatomycosis or tinea. However, external aqueous patches including butenafine hydrochloride have not been developed yet.

This is because butenafine hydrochloride has low water-solubility and is difficult to disperse homogeneously in the gel paste of an aqueous patch. Furthermore, as described above, patches which include antifungal agents blended in an acrylic or a rubber-base adhesive do not provide sufficient release of free butenafine as an active ingredient from the formulations or sufficient permeation of free butenafine into the application sites.

[Patent Document 1] Japanese Patent Laid-Open Hei 7-309755
[Patent Document 2] Japanese Patent Laid-Open Hei 7-309756
[Patent Document 3] Japanese Patent Laid-Open Hei 6-211651
[Patent Document 4] Japanese Patent Laid-Open Hei 7-277975
[Patent Document 5] Japanese Patent Laid-Open Hei 10-152433
[Patent Document 6] Japanese Patent Laid-Open Hei 8-20527

DISCLOSURE OF THE INVENTION

Problems to be Solved by the Invention

In view of the above circumstances, an object of the present invention is to provide a butenafine hydrochloride-containing aqueous patch which provides excellent adherence and retention of butenafine hydrochloride blended therein on the application sites and has excellent storage stability, and exert an antifungal effect for an extended period of time.

As a result of dedicated research to solve the above problems, the inventors have newly found that an aqueous patch which provides excellent retention of butenafine hydrochloride in addition to a high level of adherence onto the application sites such as skin and nails and excellent storage stability, and exert an antifungal effect for an extended period of time could be obtained by dissolving butenafine hydrochloride in a mixed solution of glycol salicylate and propylene glycol and dispersing the resulting solution homogeneously in a hydrogel paste, and completed the present invention.

Means for Solving the Problems

Therefore, one basic embodiment of the present invention is a butenafine hydrochloride-containing aqueous patch which includes butenafine hydrochloride, glycol salicylate, and propylene glycol in a hydrogel paste.

Specifically, the present invention provides the butenafine hydrochloride-containing aqueous patch which is produced by dissolving butenafine hydrochloride in a mixed solution of glycol salicylate and propylene glycol and dispersing the resulting solution in the hydrogel paste.

More specifically, the present invention provides the butenafine hydrochloride-containing aqueous patch wherein glycol salicylate and propylene glycol are mixed in a ratio of 1:2 to 1:30. The present invention also provides the butenafine hydrochloride-containing aqueous patch wherein an amount of propylene glycol in the gel paste is 2 to 25% by weight.

In another embodiment, the present invention provides a method for producing a butenafine hydrochloride-containing aqueous patch, including the steps of: dissolving butenafine hydrochloride in a mixed solution of glycol salicylate and propylene glycol; and dispersing the resulting solution in a hydrogel paste.

Advantageous Effects of the Invention

The present invention provides an aqueous patch which includes glycol salicylate as a solubilizer for butenafine hydrochloride and additionally propylene glycol to enhance retention of butenafine hydrochloride in the stratum corneum.

Although the aqueous patch provided by the present invention shows retention of butenafine hydrochloride in the stratum corneum to a certain extent when glycol salicylate is used alone as a solubilizer for butenafine hydrochloride, the aqueous patch provides increased retention when glycol salicylate is used in combination with propylene glycol. Furthermore, the storage stability of the formulations themselves is improved by blending propylene glycol.

Therefore, the present invention provides a butenafine hydrochloride-containing aqueous patch which provides excellent retention of butenafine hydrochloride on the application sites such as skin and nails and also has excellent storage stability and is highly therapeutic. Under current circumstances where aqueous patches which contain butenafine hydrochloride have not been developed, the present invention successfully provides an effective therapeutic agent for treatment of tinea or candidiasis and this formulation has a great medical effect.

BRIEF DESCRIPTION OF THE DRAWINGS

FIG. 1 is a graph showing the result of the release assay of butenafine hydrochloride in accordance with Experimental Example 7 of the present invention.

BEST MODE FOR CARRYING OUT THE INVENTION

Butenafine hydrochloride used as an active ingredient in the present invention is a benzylamine antifungal agent and has already been clinically used as a therapeutic agent for dermatomycosis or tinea. Butenafine hydrochloride has extremely poor water-solubility even though it exists in the form of a hydrochloride.

Therefore, in order to disperse butenafine hydrochloride homogeneously in a dissolved form in the gel paste of an aqueous patch, it is necessary to dissolve butenafine hydrochloride in the gel paste by using a solubilizer.

It was found that in the aqueous patch provided by the present invention, extremely good aqueous patches could be prepared when glycol salicylate is blended as a solubilizer to dissolve butenafine hydrochloride, and additionally propylene glycol is blended to enhance the retention of butenafine hydrochloride in the stratum corneum.

One feature of the present invention lies in the use of both glycol salicylate and propylene glycol as a solubilizer for butenafine hydrochloride.

After investigation, the inventors concluded that the amount of glycol salicylate blended as a solubilizer for butenafine hydrochloride was preferably 0.5 to 5% by weight.

When less than 0.5% by weight of glycol salicylate is blended, unfavorable effects occur at the time of production, such as reduced operational efficiency due to heterogeneous dispersion of the main active ingredient, being butenafine hydrochloride, and reduced retention on the skin of butenafine hydrochloride.

On the other hand, when more than 5% by weight of glycol salicylate is blended, unfavorable effects such as decreased storage stability of the formulation itself occur.

In the present invention, it was found that the formulation which includes propylene glycol in addition to glycol salicylate as a solubilizer has enhanced drug retention in the stratum corneum and improved storage stability as compared to formulations in which glycol salicylate is used alone.

In this case, propylene glycol is preferably blended in an amount of 2 to 25% by weight. In particular, it is more preferable that 5 to 15% by weight of propylene glycol be blended in the gel paste, which in turn produces an enhanced drug retention effect.

Specifically, when the amount of propylene glycol in the gel paste is less than 2% by weight, propylene glycol may not dissolve butenafine hydrochloride sufficiently and it is difficult to disperse butenafine hydrochloride homogeneously in the gel paste. Therefore butenafine hydrochloride cannot be blended stably in the aqueous patch. Furthermore, unfavorable effects such as reduced retention on the skin of butenafine hydrochloride occur.

On the other hand, when the amount of propylene glycol in the gel paste is more than 25% by weight, the reduced gel viscosity causes poor shape retention and undesirable stickiness, and therefore an aqueous patch cannot be successfully shaped.

In the present invention, propylene glycol is combined with glycol salicylate as a solubilizer. In this case, the blending (mixing) ratio of glycol salicylate to propylene glycol is preferably in the range of 1:2 to 1:30, and more preferably it is 1:5 to 1:15.

When the mixing ratio is less than 1:2, unfavorable effects such as decreased storage stability and reduced retention on the skin of butenafine hydrochloride may occur. A mixing ratio of more than 1:30 is not preferable since the reduced gel viscosity causes poor shape retention and undesirable stickiness.

In the aqueous patch provided by the present invention, the water content in the gel paste is preferably 30 to 90% by weight, and more preferably 40 to 70% by weight.

When the water content in the gel paste is less than 30% by weight, the gel viscosity is increased excessively, and handling the gel paste in producing patches by spreading it onto a backing layer and a liner becomes difficult.

On the other hand, when the water content in the gel paste is more than 90% by weight, the reduced gel viscosity causes poor shape retention and undesirable stickiness, and therefore an aqueous patch cannot be successfully shaped.

In the aqueous patch provided by the present invention, the composition of the components other than those described above in the gel paste is not particularly limited. For example, water-soluble polymers, excipients, humectants, stabilizing agents, cross-linking agents or the like may be blended as appropriate to prepare a gel paste.

Examples of water-soluble polymers include gelatin, hydrolyzed gelatin, polyacrylic acid, polyacrylates, partially neutralized polyacrylic acid, polyacrylic acid-starch complexes, polyvinyl alcohol, polyvinylpyrrolidone, hydroxypropylcellulose, hydroxypropyl methylcellulose, methylcellulose, carmellose sodium, carboxyvinyl polymers, methoxy ethylene-maleic anhydride copolymers, and N-vinyl acetamide copolymers. They may be used singly or in a combination of two or more thereof.

The content of the water-soluble polymer in the gel paste is 3 to 20% by weight, and more preferably 5 to 15% by weight.

When the content is less than 3% by weight, shaping the patch becomes difficult because the gel viscosity is too low. When the content is more than 20% by weight, the water-soluble polymer is not sufficiently dissolved in the gel and good gel paste is not formed.

Example of the excipient include kaolin, titanium oxide, light anhydrous silicic acid, zinc oxide and the like, and may be used singly or in a combination of two or more thereof. The content of the excipient is preferably 5 to 60% by weight.

Examples of the humectant include concentrated glycerin, D-sorbitol, 1,3-butylene glycol, polyethylene glycol, pyrrolidone carboxylates and the like, and may be used singly or in a combination of two or more thereof. The content of the humectant is preferably 15 to 45% by weight.

Example of the stabilizing agent include edetates, p-hydroxybenzoic acid esters, tartaric acid and the like, and may be used singly or in a combination of two or more thereof.

Example of the cross-linking agent include polyvalent metal compounds such as aluminum hydroxide, aluminum glycinate, dihydroxy aluminum aminoacetate, synthetic hydrotalcite, metal aluminometasilicates and the like, and may be used singly or in a combination of two or more thereof.

Absorbefacients, preservatives, antioxidizing agents, plasticizing agents, emulsifiers, surfactant and the like may be blended if necessary in the aqueous patch of the present invention.

Examples of the backing layer for the aqueous patch of the present invention include porous materials, foams, woven fabrics, and non-woven fabrics those are consisted of polyethylene, polypropylene, polyvinyl chloride, polyester, nylon, and polyurethane, as well as laminated materials of the above-mentioned porous materials, foams, woven fabrics, or non-woven fabrics with the films or sheets, and the like may be used.

Example of the plastic film to cover the surface of the gel paste include polyethylene, polypropylene, polyester, polyvinyl chloride films, or those made therefrom by mold-release process using silicone.

The method for producing an aqueous patch provided by the present invention is not particularly limited, and the aqueous patch can be produced with any known production method. For example, a butenafine hydrochloride-containing aqueous patch can be prepared by spreading onto a backing layer the gel paste which has the composition as described above and includes butenafine hydrochloride dispersed homogeneously in a dissolved form and covering the surface of the paste composition with a plastic film.

EXAMPLES

Hereinafter, effects of the present invention will be described specifically with reference to Examples and Experimental Examples, but the scope of the present invention is not limited thereto.

Example 1

20 g of 20% polyacrylic acid aqueous solution, 1.2 g of tartaric acid, 15 g of concentrated glycerin, 5 g of carmellose sodium, 5 g of partially neutralized polyacrylic acid, 0.07 g of dihydroxy aluminum aminoacetate, 0.015 g of dried aluminum hydroxide gel, and purified water (quantum sufficit) were mixed homogeneously to prepare a hydrogel.

Subsequently, 1.0 g of butenafine hydrochloride, 0.1 g of methylparaben, and 0.05 g of propylparaben were dissolved in the mixed solution of 2.5 g of glycol salicylate and 15 g of propylene glycol, and then the resulting solution was dispersed homogeneously into the previously prepared hydrogel to produce a gel paste for the patch.

A patch was produced by spreading the gel paste onto a stretchy nonwoven fabric and covering the surface of the paste with a polyester film.

Examples 2 to 5 and Comparative Examples 1 to 3

The aqueous patches of Examples 2 to 5 and Comparative Examples 1 to 3 were produced based on the compositions (formulations) shown in Table 1 below in accordance with the preparation method described in Example 1.

The formulation of Example 1 is also listed in Table 1 below.

TABLE 1

| Components of the aqueous patches (wt %) | Examples | | | | | Comparative Examples | | |
|---|---|---|---|---|---|---|---|---|
| | 1 | 2 | 3 | 4 | 5 | 1 | 2 | 3 |
| Butenafine hydrochloride | 1 | 1 | 1 | 5 | 5 | 1 | 1 | 1 |
| Propylene glycol | 15 | 15 | 15 | 10 | 10 | — | 15 | — |
| Glycol salicylate | 2.5 | 1.25 | 5 | 2.5 | 5 | 5 | — | — |
| Methylparaben | 0.1 | 0.1 | 0.1 | 0.1 | 0.1 | 0.1 | 0.1 | 0.1 |
| Propylparaben | 0.05 | 0.05 | 0.05 | 0.05 | 0.05 | 0.05 | 0.05 | 0.05 |
| Concentrated glycerin | 15 | 15 | 15 | 20 | 20 | 15 | 15 | 29 |
| Carmellose sodium | 5 | 5 | 5 | 5 | 5 | 5 | 5 | 5 |
| Partially neutralized polyacrylic acid | 5 | 5 | 5 | 5 | 5 | 5 | 5 | 5 |
| Hydroxypropylcellulose | — | — | — | 0.5 | 0.5 | — | 0.5 | 0.5 |
| 20% polyacrylic acid aqueous solution | 20 | 20 | 20 | 20 | 20 | 20 | 20 | 20 |
| Tartaric acid | 1.2 | 1.2 | 1.2 | 1.2 | 1.2 | 1.2 | 1.2 | 1.2 |
| Dihydroxy aluminum aminoacetate | 0.07 | — | 0.07 | 0.07 | 0.07 | 0.07 | 0.07 | 0.07 |
| Magnesium aluminometasilicate | — | 0.075 | — | — | — | — | — | — |
| Dried aluminum hydroxide gel | — | 0.015 | — | — | — | — | — | — |
| Purified water | q.s. | q.s. | q.s. | q.s. | q.s. | q.s. | q.s. | q.s. |

Comparative Example 4

20 g of styrene-isoprene-styrene block copolymers, 20 g of hydrogenated rosin glycerol ester, 20 g of alicyclic saturated hydrocarbon resin, 15 g of polybutene, 1.0 g of dibutylhydroxytoluene, and 18 g of liquid paraffin were dissolved in 36 g of toluene. The resulting solution of an adhesive was mixed with the solution of 1.0 g of butenafine hydrochloride in 5.0 g of glycol salicylate to obtain a coating solution.

The coating solution was applied onto a polyester film so that a thickness thereof after drying became 100 μm. After drying, a polyethylene film with a thickness of 80 μm as a backing layer was laminated thereon to produce a tape.

The composition of the tape is listed in Table 2 below.

TABLE 2

| Components of the tapes (wt %) | Comparative Example 4 |
|---|---|
| Butenafine hydrochloride | 1 |
| Glycol salicylate | 5 |
| Styrene-isoprene-styrene block copolymer | 20 |
| Hydrogenated rosin glycerol ester | 20 |
| Alicyclic saturated hydrocarbon resin | 20 |
| Polybutene | 15 |
| Dibutylhydroxytoluene | 1 |
| Liquid paraffin | 18 |

Comparative Example 5

Butenafine hydrochloride was added to a mixed solution of glycol salicylate, peppermint oil, 2% sodium hydroxide solution, and lauromacrogol, and the mixture was heated to about 70 to 80° C. to dissolve butenafine hydrochloride. White petrolatum, stearyl alcohol, butyl paraoxybenzoate, and ethyl paraoxybenzoate were added to the resulting solution and dissolved with heating in a water bath, and the mixture was stirred thoroughly and held at about 70 to 80° C. To the mixture, a solution previously prepared by dissolving other components in purified water and heated to about 70 to 80° C. was added, and then the mixture was stirred until the mixture hardened, thereby producing a cream.

The composition of the cream is listed in Table 3 below.

TABLE 3

| Components of the cream (wt %) | Comparative Example 5 |
|---|---|
| Butenafine hydrochloride | 0.5 |
| Glycol salicylate | 2.0 |
| Peppermint oil | 1.0 |
| 2% sodium hydroxide solution | 3.0 |
| White petrolatum | 25.0 |
| Stearyl alcohol | 15.0 |
| Propylene glycol | 10.0 |
| Sodium lauryl sulfate | 1.5 |
| Lauromacrogol | 2.0 |
| Ethyl paraoxybenzoate | 0.025 |
| Butyl paraoxybenzoate | 0.015 |
| Purified water | 39.96 |

Experimental Example 1

Adhesion Durability Test

The formulations produced in Examples 1 to 5 and Comparative Examples 1 to 5 as described above were individually applied on finger nails, and the adhesion state and the state of undesirable stickiness after 8 hours were evaluated based on the following criteria.

<Criterion for Evaluation of Adhesion>
  ○: highly adhesive
  Δ: poorly adhesive (partially peeled off)
  X: no adhesiveness (easily peeled off)
<Criterion for Evaluation of Undesirable Stickiness>
  ○: not sticky
  Δ: slightly sticky
  X: clearly sticky These results are shown in Table 4. As is understood from the result shown in the table, the aqueous patches of Examples 1 to 5 had excellent adhesiveness and a little undesirable stickiness.

TABLE 4

| | Examples | | | | | Comparative Examples | | | | |
|---|---|---|---|---|---|---|---|---|---|---|
| | 1 | 2 | 3 | 4 | 5 | 1 | 2 | 3 | 4 | 5 |
| Adhesiveness | ○ | ○ | ○ | Δ | Δ | ○ | ○ | ○ | Δ | X |
| Undesirable stickiness | ○ | ○ | ○ | ○ | ○ | ○ | Δ | Δ | Δ | X |

Experimental Example 2

Drug Dispersibility

The drug dispersibility in the gel paste of aqueous patches produced in Examples 1 to 5 and Comparative Examples 1 to 3 as described above was observed visually or under a polarization microscope.

The result is shown in Table 5 below.

TABLE 5

| | Examples | | | | | Comparative Examples | | |
|---|---|---|---|---|---|---|---|---|
| | 1 | 2 | 3 | 4 | 5 | 1 | 2 | 3 |
| Dispersibility | Good | Good | Good | Good | Good | Good | Poor | Poor |

In the patches of Comparative Examples 2 and 3, deposition of crystals due to drug aggregation was visually observed. The drug dispersibility in these patches was very poor, and the drug was not successfully dispersed homogeneously in the gel paste.

In contrast, in the aqueous patches of Examples 1 to 5 which include glycol salicylate and propylene glycol according to the present invention, no drug aggregation was observed and the drug was dispersed well in the gel paste.

Experimental Example 3

Drug Retention Test 1

Skin was excised from the abdomen of a 7-week old male Wistar rat and mounted onto Franz diffusion cells. Patch pieces 19 mm in diameter, which were made by die-cutting the patches from Examples 1 to 3 and Comparative Examples 1 to 4, and commercially available Cream A (concentration of butenafine hydrochloride: 1%) were applied onto the rat skins. A mixed solution containing phosphate buffer with the pH of 7.4 and Polyethylene Glycol 400 (ratio of 6:4) was used as a receptor fluid. Each formulation was peeled off 8 hours after application, and the amount of butenafine which had accumulated in the rat skins was measured by high-performance liquid chromatography.

The result is shown in Table 6 below.

As is understood from the result shown in the table, the aqueous patches of Examples 1 to 3 of the present invention provided a higher level of retention of butenafine in the rat skin as compared to formulations of Comparative Examples 1 to 4. In particular, the aqueous patches of Examples 1 and 2 were excellent.

TABLE 6

| | The amount of butenafine that accumulated in the rat skin (μg/g) |
|---|---|
| Example 1 | 281.8 ± 95.1 |
| Example 2 | 293.8 ± 20.6 |
| Example 3 | 129.7 ± 30.9 |
| Comparative Example 1 | 73.1 ± 24.6 |
| Comparative Example 2 | 172.7 ± 33.2 |
| Comparative Example 3 | 129.4 ± 61.1 |
| Comparative Example 4 | 3.4 ± 0.4 |
| Commercially available Cream A | 162.3 ± 41.8 |

Experimental Example 4

Drug Retention Test 2

The patches of Examples 1 to 3 and Comparative Examples 1 to 4 or a nonwoven fabric on which a predetermined amount of commercially available Cream A had been spread were die-cut into respective pieces 19 mm in diameter and applied onto pig nails.

These were allowed to stand at 25° C. and 60% relative humidity for 48 hours. Subsequently, each formulation was removed carefully and the nail surface was wiped off with gauze dampened with methanol. Then, the amount of butenafine which had accumulated in the nail was measured by high-performance liquid chromatography.

The result is shown in Table 7.

The formulations of Examples 1 to 3 being the patches of the present invention provided a higher level of retention of butenafine in the pig nail as compared to the formulations of Comparative Examples 1 to 4 and commercially available Cream A.

TABLE 7

| | The amount of butenafine that accumulated in the nails of a pig (μg/g) |
|---|---|
| Example 1 | 112.5 |
| Example 2 | 103.1 |
| Example 3 | 88.5 |
| Comparative Example 1 | 33.5 |
| Comparative Example 2 | 60.1 |
| Comparative Example 3 | 36.8 |
| Comparative Example 4 | 1.3 |
| Commercially available Cream A | 5.1 |

Experimental Example 5

Drug Stability Test

The aqueous patches of Examples 1 to 3 of the present invention were cut into 5 cm long and 5 cm wide pieces, placed in lightproof air-tight containers, and stored at 40° C. or 50° C.

On each measurement day, pieces of formulations were removed from the air-tight containers, which had been kept under the storage conditions, and they were subjected to heat reflux extraction with methanol. After adequate cooling, the extracts were measured by liquid chromatography, and the content of drug relative to an initial amount of the drug was assessed.

These results are shown in Table 8 (stored at 40° C.) and Table 9 (stored at 50° C.).

As is understood from the results shown in the table, the aqueous patches of Examples 1 to 3 of the present invention had excellent storage stability under either of the storage conditions.

TABLE 8

| | Drug content relative to the initial amount (%) | | | |
|---|---|---|---|---|
| Stored at 40° C. | Initial amount | After 1 month | After 3 months | After 6 months |
| Example 1 | 100.0 | 100.8 | 100.7 | 100.7 |
| Example 2 | 100.0 | 102.3 | 102.3 | 102.3 |
| Example 3 | 100.0 | 99.4 | 99.4 | 99.1 |

TABLE 9

| | Drug content relative to the initial amount (%) | | | |
|---|---|---|---|---|
| Stored at 50° C. | Initial amount | After 2 weeks | After 1 month | After 2 months |
| Example 1 | 100.0 | 101.2 | 100.5 | 99.6 |
| Example 2 | 100.0 | 101.8 | 101.3 | 101.3 |
| Example 3 | 100.0 | 99.3 | 97.8 | 96.0 |

Experimental Example 6

Drug Retention Test 3

One percent butenafine hydrochloride solution was prepared by dissolving butenafine hydrochloride in propylene glycol or 50% propylene glycol aqueous solution. Each 1% solution was dropped on pig nails and the nails were allowed to stand at 25° C. and 60% relative humidity for 24 hours. Subsequently, the solution was carefully removed and the pig nail surface was wiped off with gauze dampened with methanol, and then the amount of butenafine which had accumulated in the pig nail was measured by high-performance liquid chromatography.

The result is shown in Table 10 below.

As is understood from the result shown in the table, it was shown that the solution of butenafine hydrochloride in 50% propylene glycol aqueous solution provided a significantly increased retention of butenafine hydrochloride in the pig nail as compared to a solution thereof in propylene glycol alone.

TABLE 10

| | The amount of butenafine that accumulated in the nails of a pig (μg/g) |
|---|---|
| Propylene glycol | 2.05 |
| 50% propylene glycol aqueous solution | 68.1 |

Experimental Example 7

Drug Release Test

The release of butenafine hydrochloride from formulations produced in Example 1 and Comparative Example 5 was evaluated.

USP Apparatus 5 (Paddle over Disk) was used for this test and 40% polyethylene glycol aqueous solution was used as a test solution.

The result is shown in FIG. 1.

The result shown in FIG. 1 indicates that the patch of Example 1, being the aqueous patch of the present invention, provides a higher level of release amount and faster release rate of butenafine hydrochloride than the formulation (cream) of Comparative Example 5, and accordingly, it can be proved that the aqueous patch of the present invention is very useful.

INDUSTRIAL APPLICABILITY

As described above, the present invention provides an aqueous patch which has excellent storage stability and provides excellent retention of butenafine hydrochloride blended therein onto the application sites such as skin and nails and is highly therapeutic for tinea or candidiasis.

Under the current circumstances where an aqueous patch which contains butenafine hydrochloride has not been developed, the aqueous patch has a great medical effect.

The invention claimed is:

1. A butenafine hydrochloride-containing aqueous patch, comprising butenafine hydrochloride, glycol salicylate, and propylene glycol in a hydrogel paste, wherein the patch is produced by dissolving butenafine hydrochloride in a mixed solution of glycol salicylate and propylene glycol and by dispersing the resulting solution in the hydrogel paste, and wherein glycol salicylate and propylene glycol are mixed in a ratio of 1:2 to 1:30.

2. The butenafine hydrochloride-containing aqueous patch according to claim 1, wherein an amount of propylene glycol in the gel paste is 2 to 25% by weight.

3. A method for producing a butenafine hydrochloride-containing aqueous patch, the method comprising the steps of:
    dissolving butenafine hydrochloride in a mixed solution of glycol salicylate and propylene glycol, wherein glycol salicylate and propylene glycol are mixed in a ratio of 1:2 to 1:30; and
    dispersing the resulting solution in a hydrogel paste.

* * * * *